US011965774B2

(12) United States Patent
Feraru et al.

(10) Patent No.: US 11,965,774 B2
(45) Date of Patent: Apr. 23, 2024

(54) VIBRATION DOSE MEASUREMENT APPARATUS

(71) Applicant: COVENTRY UNIVERSITY, Coventry (GB)

(72) Inventors: Andrei Mihai Feraru, Rugby (GB); James Marcus Griffin, Coventry (GB)

(73) Assignee: COVENTRY UNIVERSITY, Coventry (GB)

( * ) Notice: Subject to any disclaimer, the term of this patent is extended or adjusted under 35 U.S.C. 154(b) by 254 days.

(21) Appl. No.: 17/047,817

(22) PCT Filed: Mar. 29, 2019

(86) PCT No.: PCT/GB2019/050911
§ 371 (c)(1),
(2) Date: Oct. 15, 2020

(87) PCT Pub. No.: WO2019/202293
PCT Pub. Date: Oct. 24, 2019

(65) Prior Publication Data
US 2021/0108959 A1 Apr. 15, 2021

(30) Foreign Application Priority Data

Apr. 19, 2018 (GB) .................................... 1806393

(51) Int. Cl.
*G01H 1/00* (2006.01)
*A61B 5/00* (2006.01)
(Continued)

(52) U.S. Cl.
CPC ............... *G01H 1/003* (2013.01); *A61B 5/11* (2013.01); *A61B 5/6806* (2013.01);
(Continued)

(58) Field of Classification Search
CPC . G01H 1/003; G01H 1/04; A61B 5/11; A61B 5/6806; A61B 5/6825; A61B 5/6831
See application file for complete search history.

(56) References Cited

U.S. PATENT DOCUMENTS 9,633,433 B1 * 4/2017 Thomson ............. G06K 9/6201
11,123,013 B2 * 9/2021 Garudadri ............ A61B 5/6825
(Continued)

FOREIGN PATENT DOCUMENTS

DE          10119252 A1    11/2002
DE      102007010800 A1     9/2008
(Continued)

OTHER PUBLICATIONS

International Search Report and Written Opinion received in International Application No. PCT/GB2019/050911, dated Sep. 13, 2019, 11 pages.

Primary Examiner — Mohamed Charioui
Assistant Examiner — Christine Y Liao
(74) Attorney, Agent, or Firm — Adler Pollock & Sheehan P.C.

(57) ABSTRACT

A vibration dose measurement apparatus 10 for an operator's hand 1 comprises a sensing assembly 20 connected to a control unit 25. The sensing assembly 20 comprises an accelerometer 21, gyroscope 22, and gripping force sensor 23 and may be packaged within a protective housing (not shown). By monitoring output of the sensor assembly 20, the vibration dose experienced by the hand 1 can be estimated. In the present invention, the provision of gripping force sensor 23 allows for vibration dose measurement to be adjusted based on the output of gripping force sensor 23. This can therefore take into account the force applied by an operator in gripping machinery, which can impact significantly on the effective vibration dose.

16 Claims, 5 Drawing Sheets

(51) Int. Cl.
 *A61B 5/11* (2006.01)
 *G01H 1/04* (2006.01)
(52) U.S. Cl.
 CPC .......... *A61B 5/6825* (2013.01); *A61B 5/6831* (2013.01); *G01H 1/04* (2013.01)

(56) References Cited

U.S. PATENT DOCUMENTS

| | | |
|---|---|---|
| 2003/0163287 A1 | 8/2003 | Vock et al. |
| 2009/0192723 A1* | 7/2009 | Jonsson ................ G01H 3/14 |
| | | 702/41 |
| 2010/0174502 A1* | 7/2010 | Thompson ............. G01H 1/00 |
| | | 73/1.38 |
| 2012/0013455 A1* | 1/2012 | Holst ..................... G01H 1/00 |
| | | 73/514.01 |
| 2013/0042682 A1* | 2/2013 | Busch .................... G01H 1/003 |
| | | 73/504.12 |

FOREIGN PATENT DOCUMENTS

| | | |
|---|---|---|
| EP | 3064911 A1 | 9/2016 |
| KR | 10-1126630 B1 | 3/2012 |
| WO | 2015/175838 A1 | 11/2015 |
| WO | 2017/165757 A1 | 9/2017 |
| WO | 2019/202293 A1 | 10/2019 |

* cited by examiner

VIBRATION DOSE MEASUREMENT APPARATUS

CROSS-REFERENCE TO RELATED APPLICATIONS

This present application claims priority as a national stage application submitted under 35 U.S.C. 371 from PCT/GB2019/050911 filed Mar. 29, 2019, which claims priority from GB 1806393.3 filed on Apr. 19, 2018, the entire contents of each are hereby incorporated by reference herein.

TECHNICAL FIELD OF THE INVENTION

The present invention relates to vibration dose measurement. In particular, the present invention relates to a vibration dose measurement apparatus and the use of such an apparatus to monitor vibration doses experienced by machine operators.

BACKGROUND TO THE INVENTION

In many industrial workplaces, machine operators are required to maintain a grip on machinery in order to control operation of said machinery. As such, machine operators are exposed to vibration generated by said machinery. Prolonged exposure to vibration in this manner can lead a machine operator to develop conditions such as Vibration white finger (VWF), also known as hand-arm vibration syndrome (HAVS) or dead finger.

In view of these potential dangers, it is known to monitor vibration exposure of machine operators using vibration sensing apparatus. Typically, such apparatus may comprise an accelerometer which is attached to or positioned adjacent to an operator's hand. This can provide a quantifiable measurement of vibration exposure enabling an alarm to be output should exposure exceed a predetermined threshold. An example of such an apparatus is described in US2009/0192723. In this document, a sensor unit comprising an accelerometer is integrated into a textile support so as to hold the sensor unit close to the palm of an operator. The sensor unit can thus fit between the operator's palm and the machinery in use and thus monitor the vibration experienced by the operator.

Whilst apparatus of the type discussed above provides an insight into vibration exposure, the risk of injury is not solely related to the magnitude or duration of vibration. In many instances, the risk is also dependent upon other factors such as the position or orientation of the operator's hand or arm, the size of the operator's hand, the gripping force exerted by the operator, the direction of vibration, or variations in the vibration including direction of peak vibration or magnitude of peak vibration. The prior art apparatus is not suitable to provide additional information in relation to these potential risk factors.

It is therefore an object of the present invention to provide a vibration dose measurement apparatus that at least partially overcome or alleviate the above problems.

SUMMARY OF THE INVENTION

According to a first aspect of the present invention there is provided a vibration dose measurement apparatus suitable for use by a machine operator, the apparatus comprising: a sensor assembly; and a support operable, in use, to urge the sensor assembly toward the palm of the operator wherein the sensor assembly comprises an accelerometer operable to detect linear motion; a gyroscope operable to detect rotary motion; and a gripping force sensor operable to detect gripping force applied by the operator.

The vibration dose measurement apparatus of the present invention is thus able to monitor, in addition to the magnitude and duration of vibration exposure, the rotational component of any vibrational exposure and the gripping force applied by the operator during exposure. This can provide a more accurate assessment of the risk associated with vibration exposure than the apparatus of the prior art.

The support may be formed from any suitable flexible material. For example, the support may be formed from materials including but not limited to: spandex, synthetic fabrics, or polymers including but not limited to polyethylene terephthalate (PET), thermoplastic polyurethane (TPU) or the like.

The support may be integrated into a glove, gauntlet or the like. Alternatively, the support may comprise a body portion and one or more straps. In such embodiments, the one or more straps may be adapted to fit around the operator's hand and/or wrist to secure the support in position. The straps may be adjustable.

The support may comprise an inner surface which faces toward the operator's hand in use and an outer surface that faces away from the operator's hand in use. The inner surface may be lined with an absorbent fabric. Examples of suitable absorbent fabrics include but are not limited to any one or a combination of: adiponitrile (AND), hexamethylene diamine (HMD) or adipic acid (AA) or the like. This can increase the operator's comfort wearing the apparatus and/or may help secure the grip between the apparatus and the operator, for instance by ensuring that the operator's grip is not impeded by a sweat layer between the apparatus and their palm. Most preferably, the fabric layer complies to the relevant local legislation for sweat absorbance.

The support may comprise a sensor pocket. The sensor pocket may be adapted to accommodate the accelerometer, gyroscope and gripping force sensor. The sensor pocket may be defined by a space between two layers of the support. In use, the sensor pocket may be positioned adjacent to the palm of the operator.

The accelerometer may be a MEMS accelerometer. The gyroscope may be a MEMS gyroscope. In one embodiment, an integrated MEMS accelerometer and gyroscope is provided.

The gripping force sensor may be a strain gauge or a force-sensing resistor. Force-sensing resistors typically have lesser output calibration drift over time than strain gauges. The gripping force sensor may be operable to measure absolute griping force or variation in gripping force. The gripping force sensor may be bonded to the support. In this manner, the strain gauge is exposed to strain resulting from deformation of the support by the operator's grip. The gripping force sensor may be bonded to part of the support forming the pocket.

In other embodiments, the gripping force sensor may be bonded to a mounting substrate housed within the pocket. In such cases, the accelerometer and/or gyroscope may also be mounted to said substrate. This may define a sensing assembly. Said substrate may comprise a printed circuit board (PCB) or a flexible PCB. Said sensing assembly may be packaged within a protective housing.

The apparatus may additionally comprise a processor. The processor may be connected to the outputs of the accelerometer, gyroscope and gripping force sensor.

The processor may be operable to receive and process output signals from the accelerometer, gyroscope and gripping force sensor so as to determine whether a safe vibration dose is exceeded. This may be achieved by calculating a vibration dose from the output signals and comparing said calculated dose to a threshold dose level. The vibration dose may be the A(8) value. The A(8) value is calculated from a mathematical expression and is mandated in, for example, UK law on vibration exposure and BS EN ISO 0841, 2005. The A(8) value calculation is based on the vector sum of vibrations experienced and the time of exposure to said vibrations. The vector sum of vibrations may be calculated from the accelerometer and/or gyroscope output.

In some embodiments, the vibration dose may take into account additional sensor outputs. For instance, in some embodiments, the vibration dose calculation may be based on a modified A(8) value. The modified A(8) value may include an additional term derived from the gripping force sensor output. The additional term may be calculated from the measured gripping force and the time of exposure time to the measured gripping force. In such cases, the calculated vibration exposure dose may be greater than conventionally calculated A(8) when the output of the gripping force sensor is higher so as to take into account a greater potential for damage to an operator when they grip harder. The additional term may further take into account the position of the operator and/or the nature or localisation of the contact between the operator and a gripped tool. In such cases, the additional term may be derived from the area of the operator's body in contact with the tool and the area of the tool in contact with the operator. The respective contact areas may be treated as constants for particular operator/machine combinations. The respective contact areas may be varied in response to orientation. This enables the variation of effective vibration dose in response to the gyroscope output and thus the orientation of the operator's hand or tool. This can also enable vibratory resonances occurring at particular orientations, grip forces and vibrational frequencies to be taken into account in determining effective dose. This provides a better reflection of the hazardous impact from vibrational forces to the operator.

In some embodiments, the processor may be operable to categorise the severity of the excess vibration dose. For example, the excess dose may be classified as mild if it exceeds a first threshold but is lower than a second, higher, threshold and the excess dose may be classified as severe if it exceeds both the first and second thresholds.

The apparatus may additionally comprise a data store. The data store may be operable to store data relating to output signals from the accelerometer, gyroscope and gripping force sensor. In some embodiments, the processor may be operable to access stored data in addition to immediately output signals from the accelerometer, gyroscope and gripping force sensor when determining a safe vibration dose.

The data store may be operable to store data relating to the physical properties of the operator. Such data may include hand dimensions, age, weight, height, sex or the like. The data may include skin tissue density or estimated skin tissue density based on one or more of the parameters above. The excess dose thresholds may be varied in response to the physical properties of the user. The data store may be operable to store details of historical sensor outputs.

The apparatus may additionally comprise a dose indicator. The dose indicator may be operable in response to the processor to output an indication when it is determined that a safe vibration dose is exceeded. The indication may comprise a visual indication and/or an audio indication. Where the indication is n audio indication the dose indicator may comprise a buzzer or loudspeaker. Where the indication is a visual indication, the dose indicator may comprise one or more LEDs. The dose indicator may be operable to output an indication of the severity of the dose. In some embodiments, the dose indicator may comprise a yellow LED which may be illuminated when the excess dose is categorised as mild. In some embodiments, the dose indicator may comprise a red LED which may be illuminated when the excess dose is categorised as severe.

The apparatus may additionally comprise a communication unit. The communication unit may be operable to communicate output signals between the accelerometer, gyroscope and gripping force sensor and/or the processor to one or more external devices. Suitable external devices include but are not limited to phones, smartphones, tablets, media players, laptop computers, desktop computers, servers, machines, machine controllers or the like. The communication unit is preferably operable to communicate data wirelessly. The communication unit may operate according to any suitable data transfer format including but not limited to WiFi, Zigbee and the like.

The apparatus may additionally comprise a power source. The power source may be a battery. In addition, or as an alternative, the power source may comprise an energy scavenging unit. Suitable energy scavenging units include but are not limited to piezoelectric generators.

The processor and any one or more of the data store, dose indicator and power source may be provided together in a control unit. The processor and the one or more other components may be mounted on a PCB. The control unit may be packaged within a protective housing. Any LEDs comprising the dose indicator may be provided in apertures in the housing. The housing may be formed from any suitable material including but not limited to: thermoplastic polyurethane (TPU) or thermoplastic elastomers (TE).

The support may comprise a control unit pocket. The control unit pocket may be adapted to accommodate the control unit. The control unit pocket may be defined by a space between two layers of the support.

The control unit and sensing assembly may be connected by a wired connection. The wired connection may comprise an extendible cable. The extendible cable may comprise a conductive ribbon material or a conductive cable woven onto a stretchable fabric. The wired connection may be provided within a sheath running between the sensor pocket and the control unit pocket. The sheath may be defined by an elongate space between two layers of the support The apparatus may additionally comprise a visual sensor. The visual sensor may comprise a camera. The visual sensor may be positioned so as to capture images of the operator's skin. Typically, the visual sensor is provided in the vicinity of one or more relatively prominent blood vessels. The visual sensor or the processor may be operable to apply spatial decomposition and temporal filtering to captured images. In this manner the apparatus can provide an output indicative of the operator's blood flow.

The support may comprise a visual sensor pocket. The visual sensor pocket may be adapted to accommodate the visual sensor. The visual sensor pocket may be defined by a space between two layers of the support and provided with an aperture upon the innermost layer such that the visual sensor may capture images of the operator's skin. The visual sensor may be connected to the control unit and/or the sensing assembly by a wired connection. In some such embodiments, the wired connection and the associated sheath may run between the sensing assembly, visual sensor and control unit.

The processor may be operable to receive the signals output by the visual sensor. The signals may be processed to determine the operator's pulse rate and/or blood mass flow rate. The processor may be operable to include signals output by the visual sensor in determining the vibration dose. Additionally or alternatively, the processor may be operable to determine that a safe vibration dose is exceeded if a pulse rate or blood mass flow rate falls outside a safe threshold range. In this manner, the apparatus may be operable to take account of changes in an operator's pulse rate and/or blood mass flow rate in determining whether a safe dose has been exceeded. For instance, a high pulse rate may indicate that an operator is tiring and thus a lower vibration dose may be harmful. Additionally or alternatively, a reduction in blood mass flow rate may indicate contraction in blood vessels, particularly at the extremities of the operator's hand. Such contractions are associated with VWF, HAVS, carpal tunnel syndromes and the like. In some embodiments, the processor may be operable to compare current visual sensor output to a stored visual sensor output for a particular operator. This can provide an indication as to whether pulse and/or blood mass flow rates are varying for a given vibration dose and hence whether further investigation is warranted.

According to a second aspect of the present invention there is provided a method of monitoring the vibration dose experienced by a machine operator, the method comprising the steps of: providing the operator with a vibration dose measurement apparatus according to the first aspect of the present invention; monitoring the vibration dose detected by the apparatus; and outputting a warning if the detected dose exceeds a threshold.

The method of the second aspect of the present invention may incorporate any or all features of the apparatus of the first aspect of the invention as required or as desired.

The method may include the additional step of outputting a shut down signal to a machine where a vibration dose threshold is exceeded.

The method may include the step of storing vibration dose data relating to particular operator and/or machines. In such cases, the method may include the additional step of comparing vibration dose data to stored vibration dose data. This can help identify potential problems with operators such as poor technique or fatigue. It may also help identify potential maintenance issues for machines.

According to a third aspect of the present invention, there is provided a method of determining a vibration dose experienced by a machine operator, the method comprising the steps of: measuring the magnitude and orientation of vibration experienced by the operator; measuring the gripping force of the operator; and calculating the vibration dose from: the vector sum of the measured vibrations; the measured gripping force; and the exposure time to said vibrations and gripping force.

The method of the third aspect of the present invention may incorporate any or all features of the apparatus of the first or second aspects of the invention as required or as desired.

DETAILED DESCRIPTION OF THE INVENTION

In order that the invention may be more clearly understood embodiments thereof will now be described, by way of example only, with reference to the accompanying drawings, of which:

Figure 1:
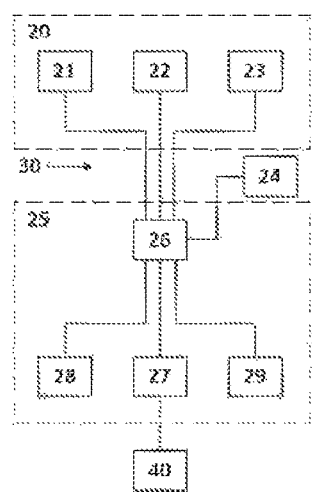
FIG. 1 is a schematic block diagram of the vibration dose measurement apparatus of the present invention.

Turning to FIG. 1, a vibration dose measurement apparatus 10 for an operator's hand 1 comprises a sensing assembly 20 connected to a control unit 25. Optionally, as is shown in FIG. 1, a separate visual sensor 24 may additionally be provided.

The sensing assembly 20 comprises an accelerometer 21, gyroscope 22, and gripping force sensor 23 and may be packaged within a protective housing (not shown). The accelerometer 21 and gyroscope 22 allow linear movement, rotational movement and orientation of the sensor assembly 20 to be detected. By monitoring the magnitude and direction of this movement, as well as the orientation of the sensor assembly 20, the vibration dose experienced by the sensor assembly 20 can be determined and hence the vibration dose received by the hand 1 can be estimated.

The accelerometer 21 and gyroscope 22 are typically MEMS devices. Optionally, a combined MEMS accelerometer and gyroscope can be used in place of separate dedicated sensors.

The gripping force sensor 23 is typically a force-sensing resistor. The gripping force sensor 23 is mounted to a substrate, typically a printed circuit board upon which the accelerometer 21 and gyroscope 22 are also mounted. As will be described in more detail below, the gripping force sensor 23 is positioned so as to experience force applied by the gripping force of the operator's hand 1. The force applied by the hand 1 can be taken into account either in calculating the vibration dose experienced by the hand 1 or in calculating a safe vibration dose threshold.

In the example of FIG. 1, the control unit 25 comprises a processor 26, a communication unit 27 and an optional data storage unit 28. Typically, each said component is mounted on a common printed circuit board. In many instances, the control unit will optionally further incorporate a power source such as a battery (not shown)

The processor 26 is operable to receive the outputs from sensors 21-24, typically by way of a common cable 30. These sensor outputs are typically processed by the processor 26 in order to determine the vibration dose and to determine whether or not the vibration dose exceeds a safe threshold. Alternatively, the sensor outputs can simply be collated by the processor 26 and passed to the communication unit 27.

Determination of vibration does may be carried out by calculating a conventional A(8) value as is known in the art. In this context:

$$A(8) = a_{hv}\sqrt{\frac{T}{T_o}} \quad (1)$$

where $a_{hv}$ is the total vibrational vector characterising a particular vibration, T is time that an operator is exposed to the vibration characterised by $a_{hv}$ and $T_o$ is a reference time value. Typically $T_o$ may be defined by reference to a working shift, say 8 hours (28,800 seconds. The value of $a_{hv}$ can be determined from the outputs of accelerometer 21 and gyroscope 22. In particular, the value of $a_{hv}$ may be determined from the square root of the sum of the root mean square (RMS) values of orthogonal vector components $a_f$. More particularly $$a_{hv} = \sqrt{a_{fx}^2 + a_{fy}^2 + a_{fz}^2} \quad (2)$$

and $$a_{fx,y,z} = \left(\frac{1}{T}\int_0^T a_{fx,y,z}^2(t)dt\right)^{1/2} \quad (3)$$

In the present invention, the provision of gripping force sensor 23 allows for vibration dose measurement to be adjusted based on the output of gripping force sensor 23. This can therefore take into account the force applied by an operator in gripping machinery, which can impact significantly on the effective vibration dose. This can be achieved by adding an additional term to equation (1) above when calculating vibration dose. accordingly, vibration dose is calculated from $$A(8) = a_{hv}\sqrt{\frac{T}{T_o}} + \frac{V_{ET}T}{\rho A_s A_h} \quad (4)$$

Where $V_{ET}$ is the vibrational energy transmitted, which can be determined from the output of the gripping force sensor 23; $\rho$ is the density of the operator's palm skin tissue (typically ~110 kgm$^{-3}$); $A_s$ is the area of the operator's skin in contact with the machinery; and $A_h$ is the area of the handle of the machinery. Typically, $\rho$, $A_s$ and $A_h$ may be treated as constants for specific operator/machinery combinations. In some embodiments, $A_s$ may be varied in response to orientation. this would reflect a difference in grip of the handle by the operator. In this context, the vibrational energy transmitted V may be calculated from the measured gripping force F by:

$$V_{ET} = F\int a_{hv}dt \quad (5)$$

In embodiments where the processor is operable to determine whether a safe vibration dose is exceeded, the apparatus 1 is provided with an optional output indicator 29, which may comprise one or more LEDs. If a safe vibration dose is exceeded, the output indicator can provide the operator with a suitable indication, such as switching on a red LED or the like.

The communication unit 28 is operable to communicate data with one or more external devices 40. This data may include data relating to the outputs of sensors 21-24. In embodiments where the processor 26 is operable to calculate a vibration dose and/or whether the vibration dose exceeds a safe threshold, the communication unit 27 may additionally communicate this data to one or more external devices 40.

The external devices 40 may include a personal device associated with the operator, such as a smartphone, or the machine that is being operated. In the case of a smartphone this may be adapted to work with the apparatus by downloading a dedicated software application. This thus allows the operator to have access to a personal record of vibration exposure. Additionally or alternatively, the smartphone may be operable to output an alarm if the vibration dose exceeds a safe threshold. In the case of a machine, in addition to outputting a local alarm to the operator, the machine may output an alarm to the operator's supervisor and/or automatically shut down.

In some embodiments, the external device 40 is a computer or server providing operator vibration dose monitoring. Such a computer or server may automatically generate alarms if a safe vibration dose is exceeded and/or output a shutdown signal to a machine where an operator has exceeded a safe vibration dose. Additionally or alternatively, such a computer or server can maintain records of vibration dose exposure for multiple operators. This can allow audits of vibration dose to take place in the future. Stored vibration dose data may also enable comparisons of vibration dose experienced by different operators to be made. This could help identify operators in need of further training. Stored vibration dose data may also be compared to quality analysis of work completed using particular machines. Unusual vibration readings may indicate that a machine requires servicing or that an operator is operating a machine unsafely or has become fatigued.

In embodiments, comprising the optional a visual sensor 24, this would typically comprise a camera 8 mounted adjacent to the operator's wrist where there are blood vessels readily visible beneath the skin. The visual sensor 24 is operable to capture a series of images of the operator's skin. Subsequently, spatial decomposition and temporal filtering is applied to the captured images so as to provide an indication of pulse rate and/or blood mass flow rate immediately below the skin. The pulse rate and/or blood mass flow rate can be taken into account in determining the apparent vibration dose experienced by the operator or in calculating a safe vibration dose threshold.

In one example, the processor 26 may be operable to compare the blood mass flow rate determined by processing the output of the visual sensor 24 to one or more threshold values or ranges. The threshold values are typically based on average biological characteristics for an operator but may be based on specific capacities of a particular operator. For instance, a typical male operator will have a blood mass of say ~7% to 8% of total body mass. Therefore, a typical male weighing 75 kg will have approximately 5.6 kg of blood. Considering that the typical wrist veins diameters of a healthy hand-arm system are 2.5 mm, the average full body blood circulation rate is 23 seconds per cycle and the average hear rate of a healthy male is 72 bpm one might expect that a typical healthy male may have a blood mass transfer into the hand of say 70 g per heart beat and thus a typical blood mass flow rate of the order of 5.04 kg of blood entering the hand per minute. Based on the above estimate, a safe vibration dose may be determined to be exceeded if the blood mass flow falls outside the threshold range of: 4.9 kg/min to 5.9 kg/min. Similarly, based on the above estimate, an immediately dangerous vibration dose may be determined to have been experienced if the blood mass flow falls outside the threshold range of: 4.6 kg/min to 6.2 kg/min.

In another example, the processor 26 may be operable to compare current visual sensor 24 output to historical visual sensor 24 output for a particular operator stored in data storage unit 28. In this context, a reduction in blood mass flow rate for the same operator for the same vibration dose may indicate contraction of blood vessels at the extremities of the operator's hand 1. Such contractions are associated with vibration damage and thus can provide an early indication that an operator may be suffering from an excessive cumulative vibration dose.

Figure 2:
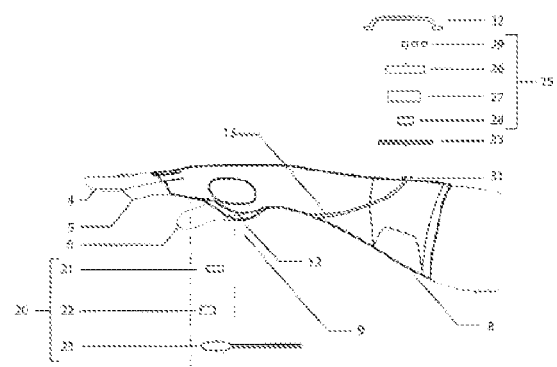
FIG. 2 is a schematic exploded diagram of a first embodiment of the vibration dose measurement apparatus of the present invention.
Figure 3A:
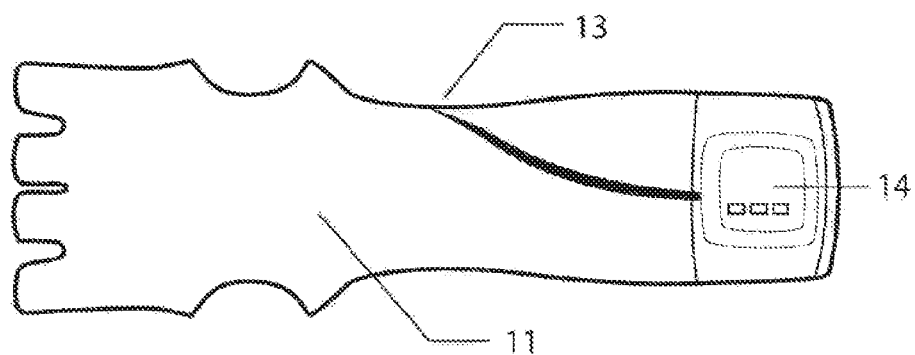
FIG. 3 shows (a) upper, (b) side and (c) lower views of the gauntlet support of the embodiment of FIG. 2.
Figure 3B:
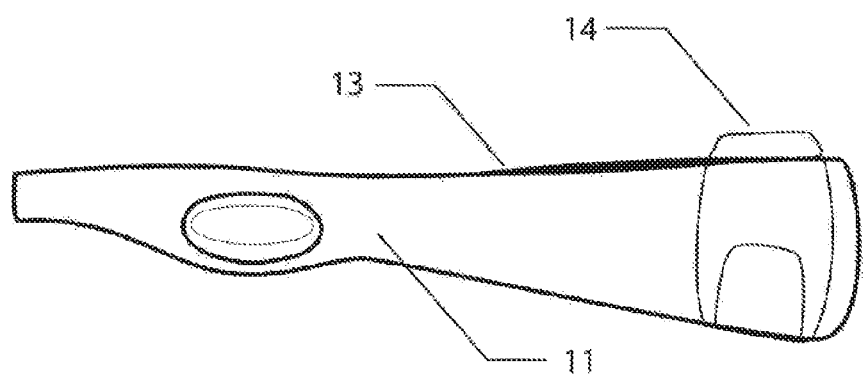
Figure 3C:
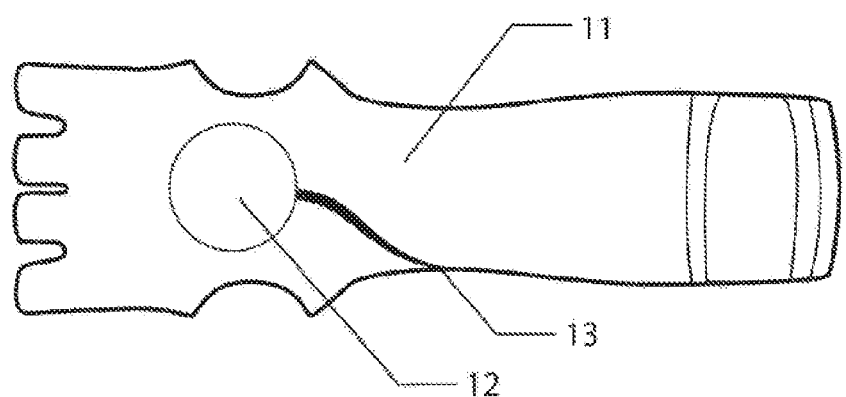

Turning now to FIGS. 2 & 3, one possible embodiment of the apparatus 10 is illustrated. In this example, the sensing assembly 20 is provided on a support 11 in the form of an extended fingerless gauntlet. The support 11 is formed from a suitable flexible material, typically a synthetic fabric or the like. The support 11 is optionally lined with an absorbent layer (not shown) for the comfort of the operator. The skilled man will appreciate that other forms of support 11 are applicable to the present invention.

The support 11 has a sensor pocket 12 formed between two layers which is held against the operator's palm 9 in use. The sensor pocket 12 thus locates the sensing assembly 20 and urges it toward the palm 9 of the operator. This enables the sensing assembly 20 to output an accurate determination of the vibrations applied to the operator's hand 1 and the gripping force applied by the operator's hand 1.

A sheath 13 formed between two layers of the support 11 runs from the pocket 12 to control unit 25. The sheath 13 can provide space for cable 30 to connect the sensing assembly 20 and control unit 25 without presenting a snagging hazard. The cable 30 can terminate at a connecter socket 31. This can facilitate ready removal of control unit 25. Beneficially, this might facilitate repair, replacement or recharging of the control unit 25 after use.

The control unit 25 can be provided in a control unit pocket 14. The control unit pocket 14 can be formed between two layers of support 11 and/or between opposing faces 32, 33 of a control unit protective housing.

Figure 4:
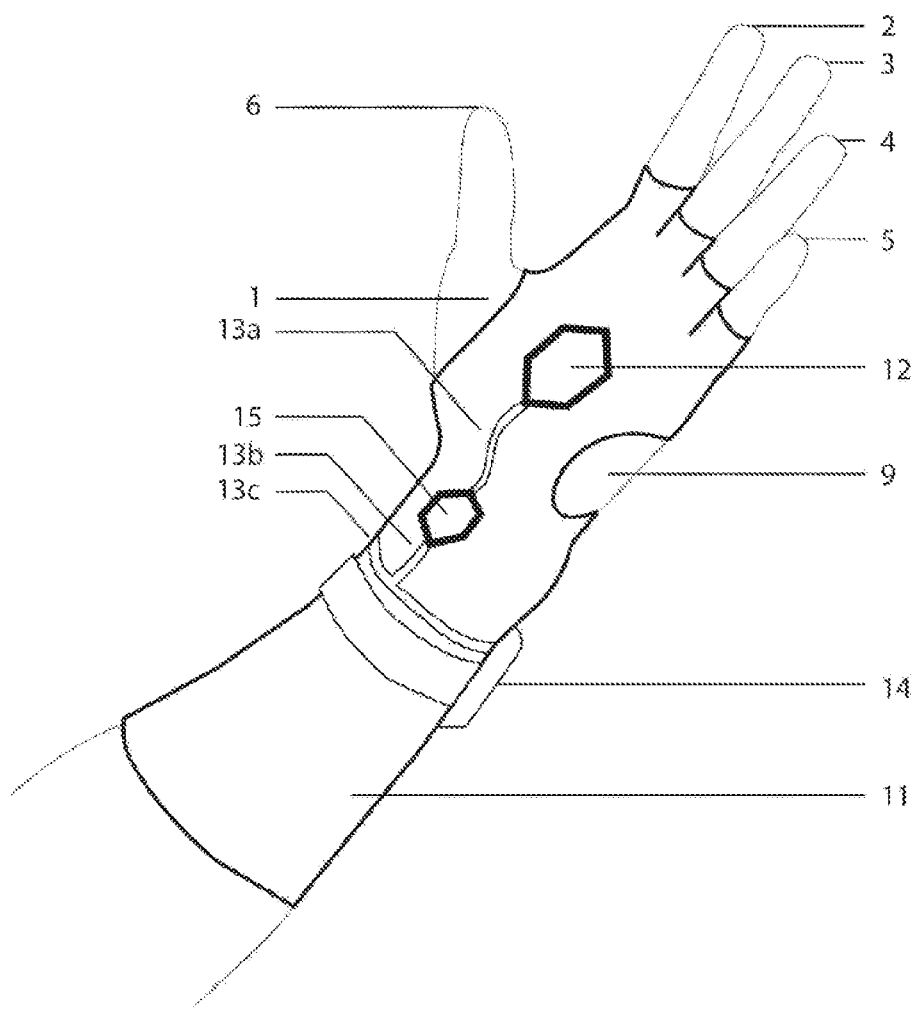
FIG. 4 shows an alternative embodiment of a vibration dose measurement apparatus according to the present invention.

In an alternative embodiment, shown in FIG. 4, the support 11 is additionally provided with a visual sensor pocket 15 adapted to house the visual sensor 24. The visual sensor pocket 15 is provided between two layers of support 11 and provides an aperture enabling visual sensor 24 to capture images of the operator's skin. Typically, this is provided in the vicinity of wrist 8 where major blood vessels to the hand 1 are close to the skin. In the example shown, sheath 13 is split into different sections 13a, 13b & 13c as required to house respective sections of cable 30.

Figure 5A:
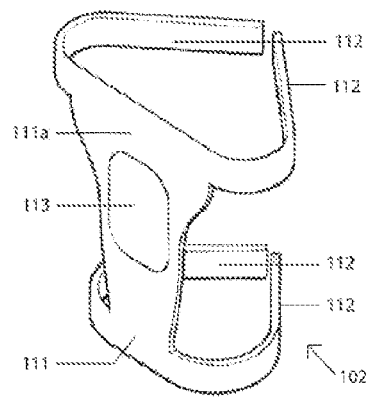
FIG. 5a shows another alternative embodiment of a vibration dose measurement apparatus according to the present invention.

Turning to FIG. 5a, another alternative vibration dose measurement apparatus 10 comprises a support 101 made up of a main body 111 and straps 112. The body 111 is substantially planer with an outward bulging pocket 113 on the front side 111a, the pocket 113 housing the sensing assembly 20 and optionally the control assembly 25. The support 101 is formed from a flexible material such as thermoplastic polyurethane (TPU) or the like. As shown in FIG. 1, the straps 112 are formed integrally with the body 111. Nevertheless, the skilled man will appreciate that the straps 112 may be formed separately to the body 111 and attached to the body 111. In such circumstances, the straps 112 may be formed of a different material to the body 111.

The straps 112 may be provided with releasable attachment and adjustment means (not shown) such that opposing straps 112 may be connected together to hold the support 101 in place. Typically, the releasable attachment and adjustment means might comprise hook and loop fabric patches, buckles, slides, clips, catches or the like.

Figure 5B:
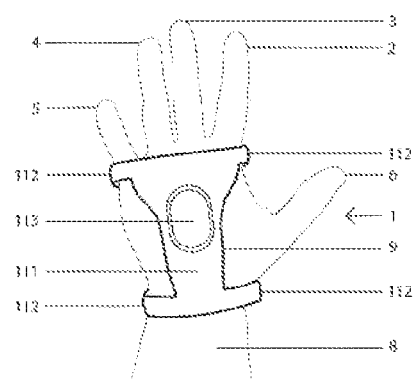
FIG. 5b shows the vibration dose measurement apparatus of FIG. 5a fitted to the hand of a machine operator.

In use, as is illustrated in FIG. 5b, the apparatus 1 is fitted to the hand 1 of an operator. The support 101 is orientated such that the recess at the rear of pocket 13 is orientated towards the palm 9 of the operator. This ensures that the sensing assembly 20 is positioned as close as possible to the centre of vibration of the hand 1. One pair of straps 112 is connected together at the wrist end 8 of the hand 1, the other pair of straps 112 is connected together at the end of the hand adjacent to fingers 2-5. The thumb 6 projects between the two pairs of straps 112. By tightening the releasable attachment and adjustment means of the straps 112, the body 111 can be urged into contact with the palm 9, further ensuring that the sensing assembly 20 experiences as close as possible a vibration dose to that experienced by the hand 1.

In order to increase the comfort and safety of the operator whilst the apparatus 1 is fitted, the support 101 or at least the side of the body 111 facing the palm 101 may be fabric lined. In particular, the fabric may be suitable for soaking up excess sweat.

Figure 6:
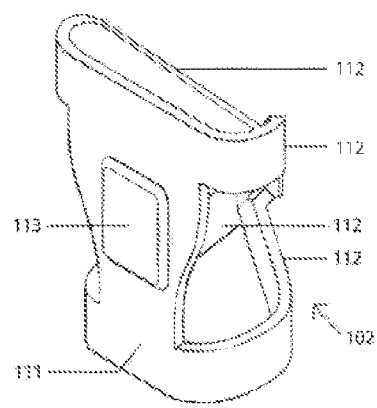
FIG. 6 shows a further alternative embodiment of a vibration dose measurement apparatus according to the present invention.
Figure 7:
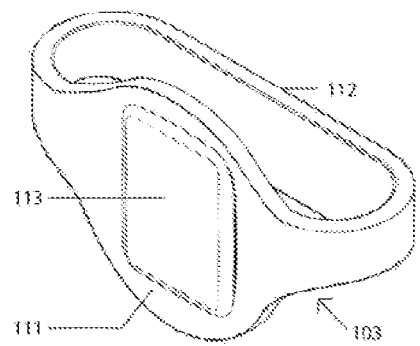
FIG. 7 shows a still further alternative embodiment of a vibration dose measurement apparatus according to the present invention.

Turning now to FIGS. 6 and 7, two alternative embodiments of the apparatus are shown. In these alternative embodiments, the key difference is that form of the support. In FIG. 6, the support 102 comprises straps 112 with an 'X' form such that all four straps 112 can be connected using a single releasable attachment and adjustment means. The embodiment of FIG. 7 provides a support 103 with only a single one-piece strap 112 and has a much smaller body portion 111. This provide a simpler and lower cost version of the apparatus. Optionally, the one-piece strap 112 in FIG. 7 may be replaced by two straps 112 connected by a releasable attachment and adjustment means.

The above embodiments are described by way of example only. Many variations are possible without departing from the scope of the invention as defined in the appended claims.

The invention claimed is:

1. A vibration dose measurement apparatus suitable for use by a machine operator, the apparatus comprising:
  a sensor assembly; and
  a support operable, in use, to urge the sensor assembly toward the palm of the operator wherein the sensor assembly comprises an accelerometer operable to detect linear motion;
  a gyroscope operable to detect rotary motion; and
  a gripping force sensor operable to detect gripping force applied by the operator,
  wherein the apparatus comprises a processor connected to the outputs of the accelerometer, gyroscope and gripping force sensor, the processor operable to receive and process output signals from the accelerometer, gyroscope and gripping force sensor so as to determine whether a safe vibration dose is exceeded, wherein the vibration dose is calculated based on a modified A(8) value including an additional term derived from the gripping force sensor output, wherein the modified A(8) value is defined by the formula $$A(8) = a_{hv}\sqrt{\frac{T}{T_o} + \frac{V_{ET}T}{\rho A_s A_h}},$$

where $a_{hv}$ is the total vibrational vector characterising a particular vibration, T is time that an operator is exposed to the vibration characterised by $a_{hv}$, $T_o$ is a reference time value, $V_{ET}$ is the vibrational energy transmitted determined from the gripping force sensor output, $\rho$ is the density of the operator's palm skin tissue, $A_s$ is the area of the operator's skin in contact with the machinery, and $A_h$ is the area of the handle of the machinery.

2. A vibration dose measurement apparatus as claimed in claim 1 wherein the support is integrated into a glove or gauntlet.

3. A vibration dose measurement apparatus as claimed in claim 1 wherein the support comprises an inner surface which faces toward the operator's hand in use and an outer surface that faces away from the operator's hand in use, the inner surface lined with fabric.

4. A vibration dose measurement apparatus as claimed in claim 1 wherein the support comprises a sensor pocket adapted to accommodate a sensing assembly defined by the accelerometer, gyroscope and gripping force sensor.

5. A vibration dose measurement apparatus as claimed in claim 1 wherein the gripping force sensor is a force-sensing resistor.

6. A vibration dose measurement apparatus as claimed in claim 5 wherein the gripping force sensor is bonded to a mounting substrate housed within the pocket.

7. A vibration dose measurement apparatus as claimed in claim 1 wherein the apparatus comprises a dose indicator operable in response to the processor to output an indication when it is determined that a safe vibration dose is exceeded.

8. A vibration dose measurement apparatus as claimed in claim 1 wherein the apparatus comprises a visual sensor operable to capture a series of images of the operator's skin.

9. A vibration dose measurement apparatus as claimed in claim 8 wherein the visual sensor or the processor is operable to apply spatial decomposition and temporal filtering to captured images so as to provide an output indicative of the operator's blood flow.

10. A vibration dose measurement apparatus as claimed in claim 9 wherein the processor is operable to determine that a safe vibration dose is exceeded if a pulse rate or blood mass flow rate falls outside a safe threshold range.

11. A vibration dose measurement apparatus as claimed in claim 9 wherein the processor is operable to compare current visual sensor output to a stored visual sensor output for a particular operator.

12. A method of monitoring the vibration dose experienced by a machine operator, the method comprising the steps of: providing the operator with a vibration dose measurement apparatus comprising: a sensor assembly; and a support operable, in use, to urge the sensor assembly toward the palm of the operator wherein the sensor assembly comprises an accelerometer operable to detect linear motion; a gyroscope operable to detect rotary motion; and a gripping force sensor operable to detect gripping force applied by the operator; monitoring the vibration dose detected by the apparatus; and outputting a warning if the detected dose exceeds a threshold, wherein the vibration dose the vibration dose is calculated based on a modified A(8) value including an additional term derived from the gripping force sensor output, wherein the modified A(8) value is defined by the formula $$A(8) = a_{hv}\sqrt{\frac{T}{T_o}} + \frac{V_{ET}T}{\rho A_s A_h},$$

where $a_{hv}$ is the total vibrational vector characterising a particular vibration, T is time that an operator is exposed to the vibration characterised by $a_{hv}$, $T_o$ is a reference time value, $V_{ET}$ is the vibrational energy transmitted determined from the gripping force sensor output, $\rho$ is the density of the operator's palm skin tissue, $A_s$ is the area of the operator's skin in contact with the machinery, and $A_h$ is the area of the handle of the machinery.

13. A method as claimed in claim 12 wherein a visual sensor is operable to capture images so as to determine an operator's pulse rate or blood mass flow rate and it is determined that a safe vibration dose is exceeded if a pulse rate or blood mass flow rate falls outside a safe threshold range.

14. A method as claimed in claim 12 including the step of outputting a shut down signal to a machine where a vibration dose threshold is exceeded.

15. A method as claimed in claim 12 including the step of storing vibration dose data relating to particular operator and/or machines.

16. A method as claimed in claim 15 including the additional step of comparing vibration dose data to stored vibration dose data to identify potential problems.

* * * * *